United States Patent [19]

Donohue et al.

[11] 4,447,645

[45] May 8, 1984

[54] PROCESS FOR PURIFICATION OF P-HYDROXYMETHYLBENZOIC ACID

[75] Inventors: John A. Donohue, Elmhurst; James O. Knobloch, Naperville; Bruce Petty-Weeks, Naperville; Steven A. Cerefice, Naperville, all of Ill.

[73] Assignee: Standard Oil Company, a corporation of Indiana, Chicago, Ill.

[21] Appl. No.: 445,659

[22] Filed: Nov. 30, 1982

[51] Int. Cl.$^3$ .............................................. C07C 69/76
[52] U.S. Cl. ...................................... 562/473; 560/64
[58] Field of Search ........................... 562/473; 560/64

[56] References Cited

U.S. PATENT DOCUMENTS 2,811,548 10/1957 Ham et al. ............................ 562/473
4,220,753 9/1980 Cerefices et al. ....................... 560/64

FOREIGN PATENT DOCUMENTS 2428878 2/1976 Fed. Rep. of Germany ........ 560/64

Primary Examiner—Paul J. Killos
Attorney, Agent, or Firm—William C. Clarke; William T. McClain; William H. Magidson

[57] ABSTRACT

Disclosed is a process for purification of p-hydroxymethylbenzoic acid containing 4-carboxybenzaldehyde, p-toluic acid and terephthalic acid impurities.

9 Claims, No Drawings

PROCESS FOR PURIFICATION OF P-HYDROXYMETHYLBENZOIC ACID

FIELD OF THE INVENTION

This invention relates to a process for the production of a resinous substantially homopolymeric p-methylenebenzoate, which comprises polymerizing p-hydroxymethylbenzoic acid containing no more than about 10% by weight terephthalic acid and no more than about 0.3% by weight total 4-carboxybenzaldehyde and p-toluic acid impurities under polycondensation and melt polymerization conditions in the presence of a suitable catalyst with the proviso that when total concentration of 4-carboxybenzaldehyde terephthalic acid and p-toluic acid impurities is more than about 0.6 (wt.)%, a glycol is present in a concentration sufficient to theoretically react with substantially all of the carboxyl equivalents of the terephthalic acid.

BACKGROUND OF THE INVENTION

This invention relates to a process for the production of a resinous substantially homopolymeric poly(p-methylenebenzoate), which comprises polymerizing p-hydroxymethylbenzoic acid containing no more than about 10% by weight terephthalic acid and no more than about 0.3% by weight total 4-carboxybenzaldehyde and p-toluic acid impurities under polycondensation and melt polymerization conditions in the presence of a suitable catalyst with the proviso that when the total concentration of 4-carboxybenzaldehyde, terephthalic acid and p-toluic acid impurities is more than about 0.6 (wt.)%, a glycol is present in a concentration sufficient to theoretically react with substantially all of the carboxyl equivalents of the terephthalic acid impurities.

p-Hydroxymethylbenzoic acid is believed to have been first prepared as early as 1872 by free-radical bromination of p-toluic acid to p-bromomethylbenzoic acid, hydrolysis with aqueous barium hydroxide and subsequent purification by recrystallization from water. Other methods for the preparation of p-hydroxymethylbenzoic acid and/or methyl p-hydroxymethylbenzoate have since been discovered, including:

(a) Hydrolysis of p-toluic acid derivatives functionalized at the benzylic position, such as p-halomethylbenzoic acid and esters.

(b) Hydrolysis of p-halomethylbenzonitriles, p-hydroxymethylbenzonitrile and p-chlorotoluyl chloride.

(c) Oxidation of p-xylene and substituted p-xylenes, such as p-hydroxymethyltoluene, p-acetoxymethyltoluene and p-xylenediol, and oxidation of p-toluic acid, p-tolualdehyde, and derivatives.

(d) Chloromethylation of benzoic acid and toluene derivatives.

(e) Carboxylation of p-halotoluene compounds via lithium salts.

(f) Disproportionation of terephthaldehyde (Cannizzaro reaction).

(g) Polarographic reduction of dimethyl terephthalate.

(h) Electrochemical reduction of terephthalic acid in aqueous solution.

(i) Hydrolysis of the ester prepared by diborane reduction of monomethylterephthalate.

However, by whatever method prepared, p-hydroxymethylbenzoic acid must be substantially free from by-products such as 4-carboxybenzaldehyde and p-toluic acid when it is to be used in polycondensation reactions, such as in the preparation of polyesters. Most of the known processes for preparation of p-hydroxymethylbenzoic acid do not yield the acid substantially free from by-products. p-Hydroxymethylbenzoic acid is extremely difficult to purify, especially from 4-carboxybenzaldehyde and terephthalic acid. High purity (99.7+%) p-hydroxymethylbenzoic acid has been obtained by recrystallization of crude products which did not originally contain any 4-carboxybenzaldehyde, but, in general, with the exception of the diborane method, reported syntheses, such as hydrolysis of p-halomethylbenzoic acid and derivatives and oxidations of p-toluic acid, are not selective enough. These reactions give products that contain 4-carboxybenzaldehyde and terephthalic acid, which cannot be reduced to levels below 1-2% by usual purification methods.

The extent of the problem was recognized at least as far back as 1958 when Ludwig, Ramm and Wiegand, J. prakt. Chem. (4)6, 103 (1958) stated, "presently known syntheses of p-hydroxymethylbenzoic acid offer no possibilites of producing this hydroxycarboxylic acid commercially, so that production of a polyester fiber from p-hydroxymethylbenzoic acid on a large scale in the foreseeable future is unlikely." This conclusion was reached upon the basis of low molecular weight polymers of p-hydroxymethylbenzoic acid with viscosities of 0.2–0.4, a glass transition temperature (Tg) of 90° C. and melting points of from 205° to 250° C. The polymers were compared to poly(ethyleneterephthalate) of inherent viscosity 0.6–1.0 deciliters/gram (dl/g) in a 60/40 phenol/tetrachloroethane solvent at 30° C., with a Tg of 73° C. and a melting point of 265° C.

Procedures also exist for the preparation of m-hydroxymethylbenzoic acid. These syntheses are analogous to those described for preparation of p-hydroxymethylbenzoic acid and methyl p-hydroxymethylbenzoate and which have been shown to be unsuitable for preparation of high-purity monomer. These methods give products, i.e., m-hydroxymethylbenzoic acid and methyl m-hydroxymethylbenzoate, contaminated with meta-toluic acid, 3-carboxybenzaldehyde and carboxylic acid impurities that are difficult to remove.

Preparations of poly(p-methylenebenzoate) having an inherent viscosity of from about 0.58 to 1.5 dl/g are known. As taught in U.S. Pat. Nos. 4,130,719 and 4,182,847, incorporated herein by reference, the polymers are formed by a process comprising (a) the formation of a prepolymer from the methyl ester, the acid, or the acetate derivative of the acid, (b) the polycondensation of the prepolymer in the melt under vacuum, and (c) polymerizing the polycondensation product in the solid state. Maximum inherent viscosity (dl/g) obtained with use of the ester, methyl p-hydroxymethylbenzoate, in a two-step polymerization, by formation of a prepolymer and melt polycondensation of the prepolymer under vacuum, as taught by U.S. Pat. No. 4,130,719 and confirmed in Example I of the instant specification, is about 0.50–0.59 dl/g. These processes suffer from the problems that either the ester or the acetate derivative must be prepared first, and a three-step polymerization procedure is required to obtain an inherent viscosity greater than 0.50–0.59 dl/g.

Poly(p- and m-methylenebenzoate) are useful polymers with properties suitable for applications in film and fiber, foams, reinforced plastic objects and engineering plastics as will be apparent upon reading of the specification.

Poly(p-methylenebenzoate) having an inherent viscosity of at least 0.6 dl/g is suitable for preparation of fibers and films. Interpolymers or blends of poly(ethyleneterephthalate), poly(butyleneterephthalate) and poly(m-methylenebenzoate) with poly(p-methylenebenzoate) which has an inherent viscosity of at least 0.6 dl/g, are also suitable for preparation of fibers and films. In general, any polyester of the structural formula

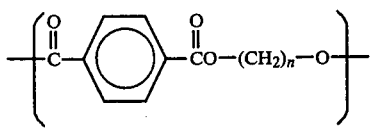

wherein n is a whole number of from 2 to 20 can be an interpolymer or blended with poly(p-methylenebenzoate) or poly(m-methylenebenzoate). For economic reasons, interpolymers or blends of poly(p-methylenebenzoate) with a polymer comprising poly(ethyleneterephthalate), poly(butyleneterephthalate) or poly(m-methylenebenzoate) are preferred. Interpolymers or blends can be in a weight ratio of from about 99.1:0.9 to about 5:95, poly(p-methylenebenzoate) to the other component or components.

An interpolymer is defined as a composition intermediate between a physical blend of two or more polymers and a totally random copolymer. Interpolymers are considered to result from the interchange reactions which occur when two or more polyesters are introduced into a melt reaction at a melt temperature wherein the weight percentage of each and reaction time cause polymer interaction between and among components.

Poly(p-methylenebenzoate) having an inherent viscosity of at least 0.6 dl/g is suitable for the preparation of molded parts, as an engineering plastic, having a tensile impact strength of at least 100 psi, according to ASTM D-1822.

In one aspect, this invention resides in a two-step polymerization process, instead of a three-step process, for the economical preparation of poly(p-methylenebenzoate) directly from p-hydroxymethylbenzoic acid which originally contained levels of 4-carboxybenzaldehyde, terephthalic acid and toluic acid which heretofore made the p-hydroxymethylbenzoic acid unusable for preparation of poly(p-methylenebenzoate) having an inherent viscosity of at least 0.6 dl/g. The invented process, because the acid is used as the monomer, avoids the necessity of preparing either the methyl ester or the acetate derivative.

In another aspect this invention resides in a two-step method of producing high viscosity poly(p-methylenebenzoate) having an inherent viscosity of at least 0.6 dl/g from p-hydroxymethylbenzoic acid from partially purified crude p-hydroxymethylbenzoic acid.

The melt polymerization of the acidic p-hydroxymethylbenzoic acid monomer compared to the polymerization of methyl p-hydroxymethylbenzoate or the acetate of p-hydroxymethylbenzoic acid was expected to form dibenzylethers and hydroxy/diacid structures which would cause branched-chain and cross-linked polymers which would have limited molecular weight and inferior mechanical properties. The acidity of p-hydroxymethylbenzoic acid was expected to catalyze side reactions of p-hydroxymethylbenzoic acid to form undesirable products. Surprisingly, the physical properties of poly(p-methylenebenzoate) prepared by this invention via a two-step process from p-hydroxymethylbenzoic acid are identical to those of poly(p-methylenebenzoate) prepared via a three-step process from methyl p-hydroxymethylbenzoate.

4-Carboxybenzaldehyde and p-toluic acid, both of which occur in the reduction of terephthalic acid to p-hydroxymethylbenzoic acid, and residual terephthalic acid act as polymer chain terminators in polymerization of p-hydroxymethylbenzoic acid to poly(p-methylenebenzoate). Low molecular weight, as measured by inherent viscosity, due to shortened polymer chains, results from the presence of these three chain terminators in amounts greater than about 0.6 (wt)%.

Monocarboxylic acid impurities, such as 4-carboxybenzaldehyde and p-toluic acid, act as polymer chain terminators in the polymerization of p-hydroxymethylbenzoic acid. From mathematical calculations, a combined level of about 0.3 (wt)% of monocarboxylic acid impurities will limit molecular weight of the polymer chain and give a polymer with inferior mechanical properties and an inherent viscosity of less than about 0.6 dl/g.

Terephthalic acid impurities in p-hydroxymethylbenzoic acid create a stoichiometric imbalance of hydroxyl and carboxylic acid units such that the resultant polymer has a predominance of carboxylic acid end groups and therefore molecular weight development is limited. Terephthalic acid can be incorporated into any location of the polymer chain but 4-carboxybenzaldehyde and p-toluic acid are located at the polymer chain ends. As a result, higher levels of terephthalic acid impurity can be tolerated.

It has been found that addition of a glycol to p-hydroxymethylbenzoic acid containing terephthalic acid, of up to about 10 (wt)% and no more than 0.3 (wt)% of 4-carboxybenzaldehyde and p-toluic acid impurities results in a high molecular weight polyester having an inherent viscosity of at least 0.6 dl/g. A molar excess of glycol to terephthalic acid within the range of from about 1:1 to 5.0:1 is added. The resultant copolymer can be used as an engineering plastic, either alone or reinforced with suitable material, such as glass fibers, glass beads, etc., or as a structural foam, a film or a fiber. The economic advantages of the instant invented process are considerable since costly purification techniques are unnecessary to prepare a copolymer with useful properties.

Copolyesters of p-methylenebenzoate are known. U.S. Pat. No. 4,130,719 teaches the preparation of copolyesters from dimethyl terephthalate, ethylene glycol and high-purity methyl p-hydroxymethylbenzoate. The copolyesters so obtained are taught as useful in applications where poly(ethyleneterephthalate) is used but where higher impact strength is needed.

Accordingly, it is an object of this invention to prepare poly(p-methylenebenzoate) directly from the acid in a two-step process to give a polymer having an inherent viscosity (I.V.) greater than 0.6 dl/g without the necessity of hydrolyzing the ester or acetoxylating the p-toluic acid methyl ester. If desired, a polymer of very high I.V., up to 1.5 dl/g, can be obtained by solid state polymerization.

It is a further object of this invention to develop a method for utilizing monomers of p-hydroxymethylbenzoic acid containing terephthalic acid in copolyesters having useful properties without the necessity of further purification of the p-hydroxymethylbenzoic acid to remove terephthalic acid. It is a further object of this invention to develop a method for producing copolyesters of p-hydroxymethylbenzoic acid having an inherent viscosity of at least 0.6 dl/g without the necessity of purifying the p-hydroxymethylbenzoic acid of terephthalic acid. Other objects will become apparent upon further reading of the specification.

The process of the instant invention can also be used to prepare poly(m-methylenebenzoate) directly from m-hydroxymethylbenzoic acid.

SUMMARY OF THE INVENTION

This invention relates to a process for the production of a resinous substantially homopolymeric poly(p-methylenebenzoate), which comprises polymerizing p-hydroxymethylbenzoic acid containing no more than about 10% by weight terephthalic acid and no more than about 0.3% by weight total 4-carboxybenzaldehyde and p-toluic acid impurities under polycondensation and melt polymerization conditions in the presence of a suitable catalyst with the proviso that when total concentration of 4-carboxybenzaldehyde terephthalic acid and p-toluic acid impurities is more than about 0.6 (wt.)%, a glycol is present in a concentration sufficient to theoretically react with substantially all of the carboxyl equivalents of the terephthalic acid.

DETAILS OF THE INVENTION

Poly(p-methylenebenzoate) is prepared with inherent viscosity of at least 0.6 deciliters/gram (dl/g) in a 60/40 phenol/tetrachloroethane solvent at 30° C. in a convenient manner in a two-step process from p-hydroxymethylbenzoic acid containing no more than 0.3 (wt) % of impurities. A polyester having an inherent viscosity of at least 0.6 dl/g is prepared using the crude acid in the presence of a glycol in a concentration sufficient to react with substantially all of the carboxyl equivalents of the terephthalic acid.

Preparation of crude p-hydroxymethylbenzoic acid can be by electrochemical means, wherein the acid is produced by electrochemical reduction of terephthalic acid, as is taught in commonly assigned patent application U.S. Ser. No. 319,120 and German Pat. No. 2,642,496, which are hereby incorporated by reference, or by hydrolysis (acid or alkaline) of the crude hydroxymethylbenzoic acid ester prepared by reduction of terephthalaldehydic acid methyl ester, as is taught in G.B. Pat. No. 2,023,581, hereby incorporated by reference. The acids can be purified by any one of several methods or combination of these methods, as will be disclosed later. The crude methyl ester of hydroxymethylbenzoic acid can be purified also by a combination of methods either as the acid or ester, as will be disclosed later.

The crude product of electrolysis of terephthalic acid in the presence of ammonia is the ammonium salt of p-hydroxymethylbenzoic acid which has been determined by liquid chromatographic analysis to contain typically the following impurities as weight percent of the p-hydroxymethylbenzoic acid present: terephthalic acid 5-10 (wt) %, 4-carboxybenzaldehyde 0.1-2 (wt) %, p-toluic acid 0.1-0.5 (wt) %, and ring-reduced derivatives 1.0-5.0 (wt) %. These acids also are present as the ammonium salts.

Purified p-HMBA containing no more than 0.3 wt)% impurities of 4-carboxybenzaldehyde and p-toluic acid and no more than about 10 (wt)% of terephthalic acid is polymerized in a simple two-step process to obtain a polymer having an I.V. of at least 0.6 dl/g, preferably within the range of from about 0.6 dl/g to about 0.9 dl/g, more preferably within the range of from about 0.7 dl/g to 0.8 dl/g.

In general, the polymerization reaction is carried out with a monomer catalyst mixture wherein the catalyst comprises about 1.0 to 0.001% by weight of the monomer. Typical catalysts which can be used are tetrabutyl titanate, tetraisopropyl titanate, dibutyl tin maleate, butyl stannoic anhydride and dihydroxy tin chloride. A preferred catalyst is butyl stannoic anhydride because of activity.

The pressure at which the process is operated is not critical and it has been found convenient to conduct at least part of the process at atmospheric pressure. However, since the reaction results in the production of water as a volatile condensation product, it has been found advantageous to complete the reaction under reduced pressure to assist the removal of such volatile materials.

The reaction is preferably effected in the absence of air which can cause some degradation and undesirable coloring of the products, and, if desired, can be effected under a constant flow of an inert gas, that is, a gas which does not interfere with polymerization reaction, for example, nitrogen which can conveniently be passed through the reaction mixture to stir the mixture and aid the removal of the volatile reaction products.

The reaction is conveniently effected in two stages, the first stage being to drive off any initial volatile condensation products and to obtain a homogeneous melt; and the second stage, at a higher temperature than the first stage, to continue the polymerization to a desired degree of conversion.

In general, reactions are run at a temperature of from about 100° to about 300° C. under an inert gas as a sweep for a period of from about 0.5 to about 10 hours. Preferred conditions are 150° to 200° C. for 120 minutes under a nitrogen sweep gas. Partial vacuum of about 600 to about 100 mm Hg is then applied for a period of about 0.1 to about 10 hours, preferred 0.25 to 4 hours, and full vacuum, 5.0 to 0.01 mm Hg, applied for about 1 to about 8 hours with the temperature maintained at 250° to 310° C. The product, which is a melt, is removed from the reactor, cooled to a solid state under 100° C. and finely ground to about 20 to 40 mesh. The material can then be solid state polymerized by heating at 150° to 250° C. at 50-0.1 mm Hg vacuum for 6 to 24 hours. Preferred conditions are 220° C. at 0.5 mm Hg for 8-16 hours. Inherent viscosity (I.V.) is measured in deciliters/gram (dl/g) in a 60/40 phenol/tetrachloroethane solvent at 30° C.

In more detail, polymerization conditions and ranges for preparing copolyesters from p- or m-hydroxymethylbenzoic acid (p-HMBA or m-HMBA) containing carboxylic acid impurities are the same as when using highly purified p-HMBA or m-HMBA.

The polymerization reaction is carried out with a monomer catalyst mixture wherein the ratio of catalyst to monomer is 1.0 to 0.001% by weight. Typical catalysts which can be used are tetrabutyl titanate, tetraisopropyl titanate, dibutyl tin maleate, butyl stannoic anhydride and dihydroxy tin chloride. A preferred catalyst is butyl stannoic anhydride because of activity.

The catalyst preferably is added at the start of the first stage. During the first stage, p-HMBA is heated above the melting point of p-HMBA, (184° C.) up to 265° C. at atmospheric pressure under an inert atmosphere for approximately 110 minutes. Water is removed via distillation. The reaction can be run at increased pressure or at sub-atmospheric pressure.

The glycol preferably is added concurrently with the catalyst during the first stage of the polymerization. The glycol has the general structure:

HO—R'—OH where R' is selected from the group consisting of —$(CH_2)_n$— wherein n is a whole number from 2 to 20, cycloaliphatic moieties of from 4 to 20 carbon atoms, and aliphatic aryl moieties of from 7 to 20 carbon atoms. The preferred glycol is ethylene glycol. A molar excess of glycol to terephthalic acid is added in the range of 1:1 to 5.0/1 (preferably 1.5/1) since the excess glycol will be removed during the polycondensation stage. The excess glycol compensates for any loss of glycol due to volatility prior to incorporation into the polymer structure.

In order to facilitate a clear understanding of the invention, i.e., the process for preparing polymers and interpolymers of poly(p-methylenebenzoate) directly from p-hydroxymethylbenzoic acid by catalytic polymerization of the acid, the following specific embodiments are described in detail. It should be understood, however, that the detailed expositions of the process, while indicating preferred embodiments, are given by way of illustration only since various changes and modifications within the spirit and scope of the invention will become apparent to those skilled in the art from this detailed description.

EXAMPLE I

This example illustrates the more severe conditions required to polymerize the methyl ester, methyl p-hydroxymethylbenzoate, compared to Example II wherein the acid, p-hydroxymethylbenzoic acid, is polymerized.

A prepolymer was prepared by placing 834.0 g. of methyl p-hydroxymethylbenzoate into a one liter 3-neck round bottom flask. The flask was equipped with a Teflon stirring paddle, a distilling head, and a thermometer. The flask was heated to 100° C. whereafter 2.5 g. of dibutyl tin maleate catalyst was added. When the contents of the flask reached 150° C. methanol was evolved. Over a 90 minute period, the temperature of the reaction was raised from 150° C. to 250° C. at such a rate as to maintain a moderate distillation of methanol. Vacuum (150 mm. Hg) then was applied for 5 minutes to remove any remaining methanol and the reaction product was poured onto an aluminum pan, cooled, and broken. The inherent viscosity of the 675.3 g of white product was 0.16 dl/g.

Melt polycondensation of the above product (651.4 g.) was carried out in a one liter resin kettle equipped with a stirrer and heated with an oil bath. Polycondensation was conducted for two hours at 272° C. oil bath temperature and 0.22-0.30 mm. Hg vacuum. The inherent viscosity of the resulting light yellow polyester (567.0 g.) was 0.58 dl/g.

A sample of the melt polymerized polyester was polymerized in the solid state at 240° C. with a nitrogen sweep for the times shown in Table I. The resultant inherent viscosity reached a value of 0.91 dl/g. after 32 hours of solid state polymerization time.

TABLE I

| Solid State Polymerization of Melt Polymer | |
|---|---|
| Time (Hours) | Inherent Viscosity (dl/g.) Melt Polymer |
| 0 | 0.58 |
| 4 | 0.69 |
| 8 | 0.75 |
| 16 | 0.81 |
| 24 | 0.84 |
| 32 | 0.91 |

The physical properties of poly(p-methylenebenzoate) injection molded parts are summarized in Table II and compared with data for poly(ethyleneterephthalate) and polycarbonate. The samples to be molded were vacuum dried at 150° C. overnight and injection molded on an Arburg 220 E/150 machine. The molding conditions for poly(p-methylenebenzoate-(PPBM) were as follows: rear zone temperature, 490° F.; front zone temperature, 530° F.; injection pressure, 13,000 p.s.i.; and mold temperature, 18° F.

TABLE II

| Physical Properties of Molded Poly(p-Methylenebenzoate) and Other Polymers | | | |
|---|---|---|---|
| Physical Property | PPMB | PET[1] | PC[2] |
| Initial I.V. dl/g. (before molding) | 0.87 | — | — |
| I.V., dl/g. (after molding) | 0.73 | 0.73 | — |
| Tensile Impact, psi. | 231 | 137 | 188 |
| Izod Impact, ft-lb/in. | No break | 0.58 | 15 |
| Heat Deflection Temperature, °F., 66 psi. | 186 | 160 | 278 |
| Yield Tensile Strength, psi. | 7800 | 8200 | 9100 |
| Elongation at Yield, % | 7.3 | 6.7 | 11 |
| Ultimate Tensile Strength, psi. | 6320 | 5270 | 9430 |
| Elongation at Break, % | 120 | 410 | 110 |
| Flexural Modulus, psi. | 301,000 | 331,000 | 345,000 |
| Density, g./in.$^3$ | 1.28 | 1.34 | 1.21 |
| Hardness, Rockwell R | 113 | 127 | 115 |
| Glass Transition Temperature °C. | 94 | 74 | 145 |

[1]Poly(ethyleneterephthalate)
[2]Polycarbonate, Lexan 110.

In Table III the solvent resistance of poly(p-methylenebenzoate) having a high inherent viscosity (0.73 dl/g) is compared with the solvent resistance of polycarbonate.

TABLE III

| Solvent Resistance of Poly(p-Methylenebenzoate) (PPMB) Compared to Polycarbonate (PC) | | |
|---|---|---|
| | Observed Effect | |
| Solvent | PC | PPMB* |
| | After 5 Minutes | |
| Benzene | Soften | None |
| Toluene | Soften | None |
| Methyl Ethyl Ketone | Craze | None |
| Chloroform | Dissolve | Craze |

TABLE III-continued

Solvent Resistance of
Poly(p-Methylenebenzoate) (PPMB)
Compared to Polycarbonate (PC)

| Solvent | Observed Effect | |
|---|---|---|
| | PC | PPMB* |
| Methanol | None | None |
| Hexane | None | None |
| *After 64 Hours* | | |
| Benzene | Dissolve | None |
| Toluene | Dissolve | None |
| Methyl Ethyl Ketone | Dissolve | Slight Craze |
| Chloroform | Dissolve | Craze |
| Methanol | None | None |
| Hexane | None | None |

*I.V. is 0.73 dl/g

EXAMPLE II

This example illustrates the facile polymerization of p-hydroxymethylbenzoic acid.

The p-hydroxymethylbenzoic acid sample contained 80 ppm of terephthalic acid, 40 ppm of 4-carboxybenzaldehyde, and 80 ppm of p-toluic acid. The polymer was prepared by placing 73.0 g. of p-hydroxymethylbenzoic acid and 0.09 g. of butylstannoic anhydride catalyst in a 500 ml polymerization kettle. The kettle was blanketed with a slow stream of nitrogen. The mixture was heated at atmospheric pressure with stirring for 120 minutes at 230°–262° C., then at 262°–265° C. for 25 minutes with the pressure being reduced from atmospheric to 0.35 mm Hg., and finally at 263°–265° C. for 170 minutes at 0.24–0.50 mm Hg. The product which was tough and transparent had a 0.86 dl/g. inherent viscosity. The inherent viscosity did not appreciate after solid state polymerization for 16 hours at 220°–225° C. and 0.3 mm Hg.

EXAMPLE III

Using the injection molding conditions described in Example I, samples of PPMB from methyl p-hydroxymethylbenzoate (Hydroxy/Ester) obtained by 3-step solid state polymerization and from p-hydroxymethylbenzoic acid (Hydroxy/Acid) obtained by 2-step melt polymerization were molded. If branching/crosslinking occurred, the ductility (i.e., impact strenghts, elongation at break) would be reduced. If thermal stability was decreased, the loss of inherent viscosity would be large. A can be seen from the data in Table IV, no property was affected.

TABLE IV

| | MONOMER | |
|---|---|---|
| Property | Hydroxy/Ester | Hydroxy/Acid |
| Inherent Viscosity, dl/g | | |
| Resin | 0.63 | 0.72 |
| Molded Part | 0.63 | 0.70 |
| Izod Impact, ft-lb/in | 18 | No Break |
| Tensile Impact, psi | 279 | 316 |
| Ultimate Tensile Strength, psi | 8,100 | 8,500 |
| Elongation at Break, % | 230 | 211 |
| Heat Deflection Temp., °F., 264 psi | 175 | 175 |
| Induction Time, Minutes | 31 | 12 |

An indication of the "perfection" of a polymer backbone is known to be the rate of crystallization of the polymer. Imperfections cause a slower rate of crystallization. The rate of crystallization of PPMB from hydroxy/acid monomer was found to be faster than from hydroxy/ester monomer. Induction time of polymer prepared from the hydroxy/acid was 12 minutes. The induction time of the polymer prepared from the hydroxy/ester was 31 minutes.

EXAMPLE IV

To demonstrate the utility of the polymers of p-HMBA having an I.V. of at least 0.6 dl/g, fibers were prepared of the material. The melt spinning of poly(p-methylenebenzoate) PPMB was performed with very little difficulty. The I.V. decreased from 0.71 feed material to 0.66 fiber I.V. Fiber was obtained of reasonably good quality with a variety of spinning speeds from 250 to 1000 meters per minute. Table V gives details of the melt spinning procedure.

TABLE V

MELT SPINNING DATA POLY(p-METHYLENEBENZOATE) (PPMB)

| | Run | | | |
|---|---|---|---|---|
| | 1 | 2 | 3 | 4 |
| Extruder Temperature, °C. | | | | |
| Zone 1 | 268 | 265 | 265 | 265 |
| Zone 2 | 271 | 268 | 268 | 268 |
| Adapter | 261 | 264 | 264 | 265 |
| Melt | 271 | 273 | 273 | 273 |
| RPM | 57 | 57 | 57 | 57 |
| Melt Pump RPM | 10 | 10 | 10 | 10 |
| Pressure | | | | |
| In | 33 | 32 | 32 | 46 |
| Out | 6 | 6 | — | 6 |
| Air Quench | 1 | 1 | 1 | 3 |
| Spinning | | | | |
| Speed (m/m) | 500 | 250 | 1000 | 500 |
| Tension (cN) | 10 | 8 | 10 | 10 |
| I.V. (dl/g) | | | | |
| Feed | .71 | .71 | .71 | .71 |
| Fiber | | 0.65 | 0.65 | 0.67 |

The properties of the undrawn, as well as the drawn PPMB, are presented in Table VI. The undrawn tenacity is 0.7 grams per denier with 425% elongation. With the best draw ratio obtained of 4.0 to 1, based on godet speeds, the highest tenacity obtained is 2.1 grams per denier with 20% elongation. The crystallinity of the fiber apparently increased during the drawing process based on the change in fiber appearance from a clear undrawn fiber to an opaque white fiber after drawing. Additional efforts were made to obtain higher tenacity fiber by preparation of water quenched monofilament. With those efforts, a 2.6 gram per denier tenacity with 12% elongation was obtained.

TABLE VI

DRAWING DATA AND FIBER PROPERTIES POLY(p-METHYLENEBENZOATE) (PPMB)

| | Run | | | |
|---|---|---|---|---|
| | 1 | 2 | 3 | 4 |
| Sample | 2 | 2 | 2 | 2 |
| Denier g/9000 m | | | | |
| Undrawn | 856 | | | |
| Drawn | | 346 | 304 | 295 |
| Elongation % | 425 | 27 | 20 | 18 |
| Breaking Str. g | 625 | 611 | 640 | 588 |
| Initial Mod. g/d | | 30 | 35 | 32 |
| Tenacity g/d | 0.7 | 1.8 | 2.1 | 2.0 |
| Drawing Conditions | | | | |

TABLE VI-continued
DRAWING DATA AND FIBER PROPERTIES POLY(p-METHYLENEBENZOATE) (PPMB)

| | Run | | | |
|---|---|---|---|---|
| | 1 | 2 | 3 | 4 |
| Temperature, °C. | | | | |
| Godet 1 | | 60 | 40 | 65 |
| Platten | | 100 | 105 | 92 |
| Godet 2 | | 55 | 40 | 60 |
| Draw Ratio | | | | |
| Set | 1.0* | 3.7 | 4.0 | 3.9 |
| Actual | | 2.5 | 2.8 | 2.9 |

*Undrawn properties.

More difficulty was experienced drawing samples run at higher spinning speeds.

EXAMPLE V

Blends of poly(p-methylenebenzoate) and poly(ethyleneterephthalate) were prepared by blending the materials by tumbling and physically mixing the two components. Melt spinning blends of both 90/10 PET/PPMB and 80/20 PET/PPMB resin mixtures were prepared. Tables VII and VIII contain the melt spinning and drawing conditions, along with the fiber physical properties of the 90/10 PET/PPMB mixture. As can be seen from Table VII the 90/10 mixture is easily melt spun at a number of spinning speeds from 250 to 1000 meters/minute and with spin line tension comparable to the PET or PPMB homopolymer alone. The spinning range examined was due to equipment limitations and not to performance of the polymer blend. As shown in Table VIII, it was possible to draw the fibers after spinning with a variety of processing conditions.

TABLE VII
MELT SPINNING DATA 90/10 PET/PPMB BLEND

| | Run | | | | |
|---|---|---|---|---|---|
| | 1 | 2 | 3 | 4 | 5 |
| Extruder | | | | | |
| Temperature, °C. | | | | | |
| Zone 1 | 266 | 264 | 264 | 265 | 268 |
| Zone 2 | 261 | 262 | 262 | 262 | 262 |
| Adapter | 254 | 253 | 253 | 254 | 254 |
| Melt | 271 | 271 | 271 | 271 | 271 |
| RPM | 61 | 61 | 61 | 61 | 61 |
| Melt Pump RPM | 10 | 10 | 10 | 10 | 10 |
| Pressure | | | | | |
| In | 28 | 20 | 17 | 20 | 17 |
| Out | 8 | 7 | 8 | 8 | 7 |
| Air Quench | 1 | 3 | 1(1) | | 1 |
| Spinning | | | | | |
| Speed (m/m) | 500 | 500 | 500 | 250 | 1000 |
| Tension (cN) | 8 | 8 | 7 | 7 | 8 |
| I.V. (dl/g) | | | | | |
| Feed | 0.69 | 0.69 | 0.69 | 0.69 | 0.69 |
| Fiber | 0.64 | 0.64 | 0.63 | 0.63 | 0.65 |

(1)Ambient Air Temperature.

TABLE VIII
DRAWING AND DATA PROPERTIES 90/10 PET/PPMB BLEND

| | Run | | | | |
|---|---|---|---|---|---|
| | 8 | 9 | 10 | 11 | 12 |
| Sample | 4 | 1 | 1 | 5 | 2 |
| Denier g/9000 m | | | | | |
| Undrawn | 1277 | 629 | 629 | 304 | 612 |
| Drawn | 307 | 225 | 185 | 107 | 165 |
| Elongation % | 26 | 81 | 84 | 48 | 41 |
| Breaking Str. g | 972 | 605 | 642 | 292 | 573 |
| Initial Mod. g/d | 80 | — | — | — | — |
| Tenacity g/d | 3.2 | 2.7 | 3.5 | 2.7 | 3.5 |
| Drawing Conditions | | | | | |
| Temperature, °C. | | | | | |
| Godet 1 | 45 | 40 | 40 | 40 | 40 |
| Platten | 117 | 35 | 35 | 35 | 35 |
| Godet 2 | 45 | 40 | 40 | 40 | 40 |
| Draw Ratio | | | | | |
| Set | 8.8 | 3.0 | 4.0 | 2.7 | 4.6 |
| Actual | 4.2 | 2.8 | 3.4 | 2.8 | 3.7 |

As illustrated in Tables IX and X, it was possible to melt spin and draw the 80/20 blend of PET/PPMB without difficulty. Fiber properties of the blend compositions were acceptable.

TABLE IX
MELT SPINNING DATA 80/20 PET/PPMB BLEND

| Run | 1 | 2 | 3 | 4 | 5 | 6 |
|---|---|---|---|---|---|---|
| Extruder | | | | | | |
| Temperature, °C. | | | | | | |
| Zone 1 | 268 | 268 | 259 | 265 | 263 | 264 |
| Zone 2 | 266 | 289(1) | 269 | 268 | 263 | 262 |
| Adapter | 250 | 250 | 257 | 254 | 254 | 254 |
| Melt | 271 | 274 | 273 | 272 | 270 | 270 |
| RPM | 57 | 57 | 57 | 61 | 61 | 61 |
| Melt Pump RPM | 10 | 10 | 10 | 10 | 10 | 10 |
| Pressure | | | | | | |
| In | 13 | — | 14 | 21 | 18 | 21 |
| Out | 9 | — | 9 | 9 | 8 | 8 |
| Air Quench | 1 | 3 | 3 | 1(2) | 1 | 1 |
| Spinning | | | | | | |
| Speed (m/m) | 500 | — | 500 | 500 | 250 | 1000 |
| Tension (cN) | 7 | 8 | 8 | 8 | 7 | 9 |
| I.V. (dl/g) | | | | | | |
| Feed | 0.68 | 0.68 | 0.68 | 0.68 | 0.68 | 0.68 |
| Fiber | 0.59 | — | 0.63 | 0.63 | 0.62 | 0.62 |

(1)Poor Spinning Performance - Zone 2 temperature too hot.
(2)Ambient Air temperature.

TABLE X
DRAWING DATA AND FIBER PROPERTIES 80/20 PET/PPMB BLEND

| Run | 1 | 2 | 3 | 4 | 5 |
|---|---|---|---|---|---|
| Sample | 5 | 5 | 5 | 5 | 1 |
| Denier g/9000 m | | | | | |
| Undrawn | 1364 | 1364 | 1364 | 1364 | 600 |
| Drawn | 296 | 277 | 252 | 264 | 201 |
| Elongation % | 36 | 30 | 27 | 20 | 28 |
| Breaking Str. g | 1150 | 1200 | 1170 | 1340 | 360 |
| Initial Mod. g/d | 83 | 85 | 87 | 103 | 56 |
| Tenacity g/d | 3.9 | 4.3 | 4.7 | 5.1 | 1.8 |
| Drawing Conditions | | | | | |
| Temperature, °C. | | | | | |
| Godet 1 | 40 | 45 | 45 | 45 | 37 |
| Platten | 110 | 110 | 110 | 110 | 75 |
| Godet 2 | 50 | 50 | 50 | 50 | 40 |
| Draw Ratio | | | | | |
| Set | 4.5 | 6.0 | 8.2 | 6.9 | 3.6 |
| Actual | 4.6 | 4.9 | 5.4 | 5.2 | 3.0 |

EXAMPLE VI

To illustrate the formation of polymers from p-hydroxymethylbenzoic acid containing dicarboxylic acid impurities, the p-hydroxymethylbenzoic acid of Example II was contaminated with additional terephthalic acid as shown in Table XI. The samples were then polymerized by a procedure identical to Example II. The deleterious effect of terephthalic acid level in the absence of added glycol on PPMB inherent viscosity is obvious wherein levels of p-toluic acid and 4-carboxybenzaldehyde remained at 80 ppm and 40 ppm respectively.

TABLE XI

Effect of Terephthalic Acid Level on PPMB Inherent Viscosity

| Sample | Terephthalic Acid Level, ppm | PPMB Inherent Viscosity, dl/g. |
|---|---|---|
| 1 | 80 | 0.86 |
| 2 | 610 | 0.78 |
| 3 | 980 | 0.77 |
| 4 | 2040 | 0.74 |
| 5 | 3320 | 0.69 |
| 6 | 6340 | 0.61 |

The above data in Table XI indicate that terephthalic acid can be present in a concentration up to at least 0.6 (wt)% in the presence of p-toluic acid and 4-carboxybenzaldehyde of the above levels and an I.V. of at least 0.6 dl/g can be obtained with use of the present invented process.

EXAMPLE VII

To illustrate the effect of the addition of a glycol to p-hydroxymethylbenzoic acid containing a high level of terephthalic acid, Sample 6 from Example VI was polymerized with the addition of ethylene glycol. A mixture of 80.0 g. of Sample 6 from Example VI, 1.0 g. of ethylene glycol, and 0.12 g. of butylstannoic anhydride was polymerized by procedure identical to Example II. The copolyester had a 1.00 dl/g. inherent viscosity.

EXAMPLE VIII

To demonstrate the utility of the polymers having an I.V. of at least 0.6 dl/g, films were prepared of material having an I.V. within the range of from about 0.64 to about 0.67 dl/g. Films were prepared on a 1½ inch extruder using a conventional chill roll quench. The film thickness was 11 mils. The stretched film was stretched upon a T.M. Long film stretcher to a level of 3 times in each direction. Resulting properties are in Table V.

TABLE XII

| Film Properties of PPMB | | |
|---|---|---|
| | Unoriented | Stretched |
| Modulus, psi | 180,000 | 325,000 |
| Yield Strength, psi | 7,800 | 10,500 |
| Ultimate Strength, psi | 7,500 | 12,500 |
| Elongation at Break, % | 160 | 22 |
| Oxygen Permeability, Barrers | 0.34 | 0.14 |

Preliminary Purification Methods

It is immaterial how the p-hydroxymethylbenzoic acid (p-HMBA) is prepared so long as the acid monomer contains no more than 0.3 (wt)% of impurities comprising 4-carboxybenzaldehyde and p-toluic acid. Up to 10 (wt)% terephthalic acid can be present.

Crude p-hydroxymethylbenzoic acid is preferably prepared by the electrochemical reduction of terephthalic acid in aqueous ammonium solution, as is taught in commonly assigned U.S. Ser. No. 319,120 and German Pat. No. 2,642,496. Purification steps can be in non-sequential order, but hydrogenation to remove 4-carboxybenzaldehyde is preferably the first step. Preferential order of purification steps after hydrogenation are (a) springing the acid by flash-drying to remove water and recover p-HMBA as the acid, (b) removal of terephthalic acid by hot aqueous filtration of p-HMBA, (c) extraction with a hydrocarbon to remove p-toluic acid and (d) crystallization to obtain pure p-HMBA. A more detailed description follows. The product of the electrochemical reduction is the ammonium salt of p-hydroxymethylbenzoic acid.

In the purification of crude p-hydroxymethylbenzoic acid, the first step is preferably hydrogenation of the 4-carboxybenzaldehyde to p-hydroxymethylbenzoic acid (p-HMBA). Any suitable catalyst, such as platinum or palladium, can be used. Noble metal catalysts, such as platinum on carbon, are preferred. Typical hydrogenation processes are taught in U.S. Pat. No. 3,726,915; German Offen. No. 2,045,747; Japanese Kokai Tokkyo Koho No. 80,143,933; Belgium Pat. No. 876,860, German Offen. No. 2,709,525 and U.S. Pat. No. 4,260,817.

It should be noted that the purification processes of the present invented process can follow alternative preliminary purifications of the crude product from reduction of terephthalic acid. One procedure is to detail off the water content of the hydrogenated ammonium salt of p-HMBA, then vacuum decompose the residue to drive off the ammonia of the salts of p-HMBA at temperatures of about 115° C. and a pressure of below 3 mm Hg. An alternative procedure is to vacuum steam decompose the ammonium salts of p-HMBA at about 200° C. and 0.2 mm Hg to obtain the free p-HMBA. Treatment of the free acid by recrystallization from water can follow, if further purification is required.

Typical sublimation processes are taught in G.B. Pat. Nos. 1,078,660; 824,367; 1,107,994; and U.S. Pat. No. 3,362,989, which teach the sublimation of other carboxylic acid compounds than p-hydroxymethylbenzoic acid at temperatures much greater than used in the instant invented process.

Another alternative procedure is springing the acid by flash drying or flash heating of the ammonium salt of p-hydroxymethylbenzoic acid to yield the free acid and ammonia. The ammonium salt is decomposed. Unreacted ammonium salt can be recycled. A spray dryer can be used wherein the temperature of the inlet gas to the dryer is within the range of from about 150° C. to about 400° C. Below 150° C., conversion of the ammonium salt to free acid and ammonia is too low to be economically useful. Temperatures much above 400° C. are limited by equipment capabilities. Decomposition of the ammonium salt in the presence of steam at atmospheric pressure and temperatures of about 160° C. is a time-temperature dependent reaction which results in unsatisfactory oligomerization during extended time periods of the free acid to dimers and trimers even though yields of over 90% are obtained of the free acid.

Treatment of the free acid from flash heating by hot aqueous filtration removes terephthalic acid. The free acid obtained by decomposing the ammonium salt is dissolved in water and filtered at a temperature within the range of from about 80° C. to about 130° C., preferably from about 110° C. to about 120° C. under pressure of from about 15 to 50 psi. The terephthalic acid, being less soluble in hot water than p-hydroxymethylbenzoic acid, solubilizes to a limited amount and is removed by filtration.

p-Toluic acid contaminants can be removed from the free acids of p-HMBA by extraction with p-xylene of p-toluic acid from aqueous solutions. The extraction can be performed at temperatures within the range of from about 23° C. to about 175° C., preferably from about 23° C. to about 150° C. The p-toluic acid can be recovered from the p-xylene by conventional means, i.e., distillation, crystallization, etc. Any equivalent aromatic hydrocarbon solvent which will solubilize p-toluic acid can be used as well as p-xylene. Benzene, toluene, m-xylene, o-xylene, ethers such as ethyl ester, and aliphatic solvents such as hexane, among other solvents, can be used.

The free acid of p-HMBA in aqueous solution after extraction of p-toluic acid is thereupon obtained by crystallization by cooling. The filtrate is recycled.

An alternative procedure to obtain the free acid from the crude ammonium salt of p-HMBA is acidification with a mineral acid. The free acid, p-HMBA is dissolved in excess hot water. The slurry is filtered to remove terephthalic acid, the free terephthalic acid being less soluble in water of a temperature of 80° to 130° C. under pressure of from about 15 to 50 psi, preferably 110° to 120° C., than the free acid of p-HMBA. Cooling of the filtrate yields p-HMBA of improved purity.

Contamination of the free acid with mineral acid anion can be removed by recrystallization of the free acid of p-HMBA from water. The free acid is recrystallized at least twice from water. U.S. Pat. No. 3,534,089 teaches one-time water crystallization of the sodium salt of p-HMBA and acidification followed by a one-time water crystallization to remove impurities. At least two recrystallizations of the free acid, p-HMBA, from water have been found to be advantageous.

Purification of the crude p-HMBA can also be obtained by forming the acetate of the acid, followed by vacuum distillation, recrystallization of the acetate and acidification, as is taught in commonly assigned U.S. Pat. No. 4,182,847.

Since the acid monomer, p-hydroxymethylbenzoic acid, can also be obtained by hydrolysis of the ester of the acid, the purified acid can also be obtained by purification of the ester prior to hydrolysis of the acid.

The ester can be obtained by hydrogenating terephthaladehydic acid alkyl ester to the p-hydroxymethylbenzoic acid ester in the presence of a hydrogenation catalyst, such as palladium on carbon, as is taught in G.B. Pat. No. 2,023,581.

The hydrogenated product as the crude ester is thereupon processed to extract the impurities and to be converted to the free acid. Purification of the crude ester is accomplished by extraction with an aqueous bicarbonate solution followed by crystallization from a hydrocarbon solvent. The ester is thereupon hydrolyzed (alkaline) with caustic solution and the basic solution is thereupon hydrogenated. Sodium borohydride, as is taught in U.S. Pat. No. 4,130,719, can be used to reduce the aldehydes remaining in the solution. The free acid, p-hydroxymethylbenzoic acid, is obtained by acidification with a mineral acid. The free acid, after being recrystallized several times from water, can contain no more than 0.3 (wt)% of impurities.

Preliminary Purification Methods

Purification Example I

Use of p-HMBA is as a difunctional monomer in polycondensation reactions requires the acid be free from compounds having other functionality such as aldehydes. Catalytic hydrogenation of 4-carboxybenzaldehyde (4-CBA) to p-HMBA using a platinum on carbon catalyst achieved reduction from 2.56% of 4-CBA in crude electrochemical cell product to 0.25% and 0.05% with a second, treatment.

Two liters of crude p-HMBA, Run No. 5995-22, and 5.0 g of 5% Pt/C were charged to the one-gallon autoclave with a glass liner insert. The reactor was taken to 1000 psi $H_2$ pressure at 22°–23° C. and held at that temperature for two hours and twenty minutes. The product solution was filtered as Run No. 6023-9 and analyzed by liquid chromatography (LC). The 4-CBA level had been reduced from 2½% to 0.25%. Run No. 6023-9 was further treated at 50° C. for two hours and forty minutes using the 5% Pt/C catalyst from the first treatment. The reaction solution was filtered as above to give Run No. 6023-9-2. The LC results are shown in Table XIII below.

TABLE XIII

| | mg/ml | | | |
|---|---|---|---|---|
| | p-HMBA | TA | 4-CBA | p-Toluic |
| Cell Product Run No. 5995-22 | 94.7 | 6.0 | 2.56 | 0.12 |
| Hydrogenation Run No. 6023-9 | 93.8 | 6.0 | 0.26 | 0.13 |
| Hydrogenation Run No. 6023-9-2 | 94.0 | 6.1 | 0.05 | 0.10 |

Purification Example II

An alternative method of obtaining the ammonium salt of p-HMBA or the crude acid from electrolytic reduction of terephthalic acid in aqueous ammonium solution is by flash heating of the crude ammonium salt of the p-HMBA. A spray dryer can be utilized for this procedure. The procedure simultaneously evaporates the water and can dry the aqueous material to either the ammonium salt or decompose the salt to the free acid. The ammonia liberated is recovered for re-use. Data from four runs follow.

Run No. 1

An aqueous ammonia solution containing 15.8(wt)% p-HMBA, 1.68(wt)% terephthalic acid (TA) and 1.98 (wt)% ammonium carbonate and having a pH of 9.13 was spray dried in a pilot plant spray dryer (Stork Bowen BLSA) with inlet gas temperature 350°–360° C. and exit gas from the solids collector at 150° C. The dry solids analyzed 0.663% N (Kjeldahl), 81.7% p-HMBA, 12.3% TA, and only 0.147% p-HMBA dimer. The calculated nitrogen content for these acids present as their ammonium salts is 9.6% N. Recovered organic acids were 93% freed of accompanying ammonia.

Run No. 2

The aqueous ammonia solution of Dryer Run No. 1 was spray dried with inlet gas temperature of 250° C. and exit temperature of 120° C. Dry solids analyzed 4.29% N. (A product analysis of 9.12% N would represent 100% presence of ammonium salts.) Organic acids were freed of their ammonia to the extent of 53%.

Run No. 3

Dryer Run No. 1 was repeated drying the solution at 150° C. inlet, 80° C. exit temperature. Dry solids analyzed 6.90% N compared to 8.84% N for 100% presence of organic acids as ammonium salts. 22% of the ammonium salts were converted to free acids.

From the above dryer runs, it is obvious that the extent of ammonium salt decomposition (acidification) is determined by the drying conditions chosen.

Run No. 4

Ammonia can be eliminated by passing superheated steam through the ammonium salt of p-HMBA. However, the extended time required causes a significant portion of the p-HMBA to oligomerize to the dimer and trimer esters. This is shown in the following.

Superheated steam was passed through crude ammonium p-hydroxymethyl benzoate at atmospheric pressure. The steaming was done for 50 minutes at a temperature rising from 155°-164° C. The steam usage, weights before and after stripping, and analyses are shown in the following Table XIV. While 93.6% of the nitrogen has been stripped from the crude feed, 8.7% of the p-HMBA had been oligomerized to dimer and trimer esters.

TABLE XIV

Steam Stripping Ammonium p-Hydroxymethylbenzoate at 160-165° C., Atmospheric Pressure

| Run Numbers | Feed[a] 5995-148-S | Stripped Sample 4743-85-1 |
|---|---|---|
| Weight | 15.0 g | 12.82 g |
| Time above 155° C. | | 50 Minutes |
| Steam used | | 152.87 g |
| g/g feed | | 10.2 |
| LC Analysis Results | | |
| p-HMBA-% | 76.91 | |
| TA-% | 5.53 | 5.483 |
| 4-CBA, ppm | 1470 | 1540 |
| p-HMBA Acetate, ppm | 4320 | 4730 |
| p-Toluic Acid, ppm | 3710 | 1870 |
| Dimer Ester, ppm | 1890 | 74,800 |
| Trimer Ester, ppm | 30 | 12,000 |
| Unknowns-% | 2.41 | 3.21 |
| Nitrogen (Kjeldahl) | 6.35% | 0.475% |
| Acid No.[b] | — | 374.08 |

[a]Crude $NH_4^+$HMBA from electrochemical cell after hydrogenation to reduce 4-CBA, and evaporation of water.
[2]Theoretical acid no. for p-HMBA is 368.7 mg KOH/g.

Purification Example III

The following demonstrates purification of p-hydroxymethylbenzoic acid by vacuum sublimation to separate terephthalic acid from p-hydroxymethylbenzoic acid. The step of vacuum sublimation followed previous steps of hydrogenation over a platinum/carbon catalyst to remove the 4-carboxybenzaldehyde, spray drying to remove ammonia and water, and hot filtration in water to remove terephthalic acid.

A mixture of p-toluic acid and p-HMBA with small amounts of 4-CBA and TA was separated by sublimation at pressure below 3 mm Hg. p-Toluic acid of about 90% purity was recovered at temperatures up to about 125° C. The HMBA-rich cut was recovered at temperatures up to about 155° C. The pot residue contained up to about ⅔ of the TA. Analyses of the starting mixture and results of the sublimations by liquid chromatography are given in Table XV.

TABLE XV

Vacuum Sublimation of a Toluic Acid and p-HMBA Mixture

| Temperature °C. of Sublimation | WT % OF CHARGE | L.C. ANALYSIS (WT) % | | | |
|---|---|---|---|---|---|
| | | p-TOLUIC ACID | p-HMBA | 4-CBA | TA |
| Start | 100% | 55.4 | 45.2 | 0.28 | 0.26 |
| 114 | >30 | 99.8 | 1.0 | 0.15 | — |
| 124 | >17 | 93.7 | 8.8 | 0.47 | — |
| 142 | >10 | 3.3 | 101.3 | 0.64 | 0.08 |
| 154 | >24 | 0.5 | 105.8 | 0.17 | 0.17 |
| Pot Residue* | ~2 | 1.4 | 78 | 0.26 | 9.38 |

Pressure: Less than 3 mm Hg
*~3% of HMBA dimer

Purification Example IV

In an alternative purification, the ammonium salt of crude p-hydroxymethylbenzoic acid (p-HMBA) was purified by vacuum steam sublimation to separate the p-HMBA from terephthalic acid remaining from the electrolytic reduction. The apparatus consisted of a steam generator, a 1-liter round bottom 3-neck flask containing water equipped with a heating mantle and magnetic stirrer, an air inlet line hving a stopcock, a thermometer dipping into the water, and an exit tube connected to a steam superheater. The superheater was made of an 11-ft. coil of ¼" stainless steel tubing immersed in a heated oil bath. The superheated steam was passed through an electrically heated tube to a 500 ml sublimation flask. There it entered the solids charge through a ⅛" diameter Pyrex tube. (The sublimation flask had a thermowell extending into the solids charge.) From the sublimation flask the sublimate-water vapor stream flowed through an electrically heated borosilicate glass line to the condenser-receiver where water and p-HMBA were condensed. From this receiver the apparatus was connected to a vacuum pump through a knock-back "cold-finger" condenser and a trap. Steam pressure was measured prior to the sublimation flask.

In Run No. J-4743-28, 50 grams of partially purified p-HMBA (previously hydrogenated and hot filtered) was vacuum steam sublimed under the conditions shown in Table XVI. In Run No. J-4743-31 the cold condenser-receiver was replaced with a room-temperature one-liter resin kettle. A knock-back tube replaced the cold-finger condenser and the steam was condensed separately in a dry ice-isopropanol cold trap. The same size charge of p-HMBA was used in Run No. J-4743-31.

TABLE XVI

Vacuum Steam Sublimation of p-Hydroxymethylbenzoic Acid

| Run No. | J-4743 −28 | J-4743 −31 |
|---|---|---|
| Conditions | | |
| Steam Source | | |
| Temp., °C. | 30-30.4 | 20-21 |
| Pres. mm of Hg | 32 | 17.5-18.7 |
| Pressure, Before Flask mm of Hg | 10.2 | 5.5 |
| Sublimator Flask | | |
| Entering steam, °C. | 175-180 | 124-133 |
| Pot temp., °C. | 135 | 129-135 |

TABLE XVI-continued

Vacuum Steam Sublimation of p-Hydroxymethylbenzoic Acid

| Steam sublimate exit line, °C. | 185–198 | 188–203 |
|---|---|---|
| Pressure After Flask mm of Hg | .10 | .20 |
| Grams of Water per gram of p-HMBA sublimed | 7.4 | 2.4 |

Results
%(wt) Sublimed
LC Analysis, parts per million

| | Starting Material | −28 | | −31 | |
|---|---|---|---|---|---|
| | | Overhead | Bottoms | Overhead | Bottoms |
| Terephthalic Acid | 4110 | 2530 | 5280 | 2700 | 5210 |
| 4-Carboxybenzaldehyde | 120 | 150 | 110 | 120 | 110 |
| p-Toluic Acid | 260 | 370 | 260 | 320 | 250 |
| Dimer ester of p-HMBA | 380 | 690 | 1010 | 540 | 1020 |

Purification Example V

The following example illustrates the purification of crude p-HMBA containing toluic acid, terephthalic acid, and 4-carboxybenzaldehyde wherein the acetate of the crude p-HMBA is formed, which is thereby vacuum distilled, recrystallized from water and hydrolyzed with a mineral acid to p-hydroxymethylbenzoic acid after saponification.

Crude p-HMBA (50 g) was added to 100 ml of acetic acid (100%). The mixture was heated, and then 22 g of acetic anhydride were added. Additional 150 ml of 100% acetic acid were added with stirring at a temperature of 115° C. The mixture was filtered hot and washed with 50 ml of boiling acetic acid (100%). The filtrate was cooled overnight and then reheated with 4 ml of acetic acid (100%) to complete the reaction. The solids were discarded. The filtrate was vacuum distilled at 130° C. and about 130 mm Hg in a rotary evaporator. The residue was vacuum distilled at 12.2 mm Hg at temperatures of from about 130° C. to about 190° C., and then at about 195° C. and 9.5 mm Hg. One gram of the solidified overhead product was dissolved in 35 ml of water at reflux and allowed to cool overnight. After filtration, the resulting solids, 0.85 g, were air-dried. Also, 0.4 g of the solid overhead product were dissolved in 4 ml 5% NaOH solution and heated for one hour. The solution was cooled and acidified to an acid state with hydrochloric acid to obtain the solid p-HMBA. The solids were removed by filtration. Analyses of the feed and purified p-HMBA are in Table XVII.

TABLE XVII p-HMBA Purification - Acetate Method
L.C. Analysis %

| Treat | p-HMBA AC | p-HMBA | TA | 4-CBA | Toluic Acid |
|---|---|---|---|---|---|
| Feed - As is | — | 59.4 | 13.6 | 0.38 | 0.05 |
| Normalized | | 80.9 | 18.5 | 0.52 | 0.07 |
| Acetate - Filtered | 96.1 | 2.3 | 1.0 | 0.38 | 0.23 |
| Vacuum Distill | 96.7 | 0.09 | 0.07 | 0.05 | 0.14 |
| Recrystallize - From H₂O | 105.8 | 0.22 | 0.8 | 0.02 | 0.11 |
| Hydrolyze - NaOH.HCl | — | 88.9 | 0.10 | 0.03 | 0.06 |

Purification Example VI

The following illustrates an alternative method of purifying p-HMBA containing p-toluic acid. One method to remove p-toluic acid from crude p-HMBA is crystallizaton from water. p-HMBA cake is separated by filtration from the mother liquor. The p-toluic acid in the mother liquor is sent to waste treatment. While this method indeed removes p-toluic acid, 0.5 wt% p-HMBA (based on the weight of mother liquor) is also lost. If the mother liquor is recycled, p-toluic acid builds up on the p-HMBA cake and contaminates the product.

If p-toluic acid is selectively removed by hydrocarbon extraction the aqueous mother liquor can be recycled without loss of p-HMBA. The p-toluic acid in the p-xylene is recovered by conventional means or converted to TA by oxidation.

Three extractions of p-toluic acid were performed with p-xylene as the extracting solvent.

Extraction 1. A mixture of 50.0 g water, 11.3 g p-xylene, 0.315 g p-HMBA and 0.044 g p-toluic acid was stirred rapidly at 50° C. for 5 minutes. Stirring was stopped and the two phases allowed to separate. Both the p-xylene and aqueous phases were analyzed by High Pressure LC. The aqueous phase contained 0.306 g p-HMBA (97%) and 0.010 g p-toluic acid (22%) while the p-xylene contained 0.0008 g p-HMBA (3%) and 0.0372 g p-toluic acid (84%).

Extraction 2. A mixture of 100 g water, 21.6 g p-xylene, 3.23 g p-HMBA and 0.394 g of p-toluic acid was extracted at 80° C. in the same manner as Extraction 1. The aqueous phase contained 3.16 g of p-HMBA (98%) and 0.105 g of p-toluic acid (27%) while the p-xylene contained 0.012 g of p-HMBA (0.40%) and 0.27 g of p-toluic acid (70%).

Extraction 3. A 400 ml aqueous solution of 1.81 g of p-HMBA and 0.162 g p-toluic acid was extracted in three stages with 60 ml of p-xylene (a total of 180 ml of p-xylene) at 25° C. After the third extraction the aqueous phase was analyzed by High Pressure LC and found to contain 1.80 g of p-HMBA (99.6% recovery) and 0.017 g p-toluic acid (90% removal).

Purification Example VII

The following illustrates that in acidification of the ammonium salt crude p-HMBA, wherein water crystallization of the p-HMBA is used to obtain purified material, after acidification with a mineral acid, at least two recrystallizations are required to remove the mineral acid anion. The sodium salt of p-HMBA was used. The presence of sulfate ($SO_4^=$) ion in the filtrate was used to determine purity.

210 g of crude p-HMBA in 240 ml of water containing 4120 ppm of terephthalic acid, 50 ppm of 4-carboxybenzaldehyde and 1080 ppm of p-toluic acid were heated and refluxed with 76 ml of an aqueous solution of 50% sodium hydroxide. After the crude acid solubilized in the NaOH solution, the solution was allowed to cool over a period of 12 hours, forming crystals of sodium salt of p-HMBA. The crystals were washed with a minimum of cold water and filtered to obtain 302 g of the Na salt. The sodium salt of p-HMBA obtained by this procedure contains 5 molecules of water per molecule of sodium HMBA (NaHMBA) in the crystal. 110 g were dissolved in 300 ml H$_2$O and sulfuric acid solution was added to a pH of less than 2. After cooling overnight, the resulting crystals were collected and washed. The crystallization process was repeated. Results are in Table XVIII.

TABLE XVIII

Effects of Recrystallization

| | Treatment | SO$_4$= ppm in Filtrate |
|---|---|---|
| (A) | Acidify NaHMBA | 37,000 |
| (B) | Water Recrystallization of Solids of (A) | 3,900 |
| (C) | Water Recrystallization of Solids of (B) | 40 |
| (D) | Water Recrystallization of Solids of (C) | 2 |

The above data indicate that at least two recrystallizations are required to remove substantially all the mineral acid anion by crystallization.

What is claimed is:

1. A process for purification of p-hydroxymethylbenzoic acid containing 4-carboxybenzaldehyde, p-toluic acid, and terephthalic acid impurities wherein said p-hydroxymethylbenzoic acid is prepared as an ammonium salt by electrochemical reduction of terephthalic acid which purification process comprises:
   (a) hydrogenation of said ammonium salt in the presence of a suitable catalyst to convert said 4-carboxybenzaldehyde impurities to p-hydroxymethylbenzoic acid,
   (b) springing said p-hydroxymethylbenzoic acid from said ammonium salt,
   (c) filtration to remove said terephthalic acid impurities by hot aqueous filtration of said p-hydroxymethylbenzoic acid,
   (d) hydrocarbon extraction of said p-toluic acid impurities from p-hydroxymethylbenzoic acid by a suitable hydrocarbon solvent, and
   (e) crystallization of substantially pure p-hydroxymethylbenzoic acid from aqueous solution.

2. The process of claim 1 wherein said hydrogenation is in the presence of a platinum on carbon catalyst.

3. The process of claim 1 wherein said springing of said acid from said ammonium salt comprises feeding said salt to a spray dryer wherein inlet gas temperature of said dryer is at a temperature within the range of from about 150° C. to about 400° C.

4. The process of claim 1 wherein said springing of said acid from said ammonium salt is in the presence of a mineral acid.

5. The process of claim 4 wherein said mineral acid is sulfuric acid.

6. The process of claim 1 wherein said hydrocarbon is selected from the group consisting of p-xylene, benzene, toluene, m-xylene, o-xylene aliphatic solvents and ethers.

7. The process of claim 6 wherein said hydrocarbon is p-xylene.

8. The process of claim 6 wherein said aliphatic solvent is hexane.

9. The process of claim 6 wherein said ether is ethyl ether.

* * * * *